(12) United States Patent
Li et al.

(10) Patent No.: US 10,980,496 B2
(45) Date of Patent: Apr. 20, 2021

(54) HEART CT IMAGE PROCESSING METHOD AND APPARATUS, AND NON-TRANSITORY COMPUTER READABLE STORAGE MEDIUM

(71) Applicant: General Electric Company, Schenectady, NY (US)

(72) Inventors: Fang Li, Beijing (CN); Wei Dong, Beijing (CN)

(73) Assignee: General Electric Company, Schenectady, NY (US)

( * ) Notice: Subject to any disclaimer, the term of this patent is extended or adjusted under 35 U.S.C. 154(b) by 76 days.

(21) Appl. No.: 16/455,953

(22) Filed: Jun. 28, 2019

(65) Prior Publication Data

US 2020/0000416 A1  Jan. 2, 2020

(30) Foreign Application Priority Data

Jun. 29, 2018 (CN) .......................... 201810696810.3

(51) Int. Cl.
| | |
|---|---|
| *A61B 6/03* | (2006.01) |
| *A61B 6/00* | (2006.01) |
| *G06T 11/00* | (2006.01) |
| *G06T 7/00* | (2017.01) |

(52) U.S. Cl.
CPC .............. *A61B 6/032* (2013.01); *A61B 6/503* (2013.01); *G06T 11/003* (2013.01); *A61B 6/504* (2013.01); *G06T 7/0012* (2013.01); *G06T 2207/10081* (2013.01); *G06T 2207/30048* (2013.01)

(58) Field of Classification Search
None
See application file for complete search history.

(56) References Cited

U.S. PATENT DOCUMENTS

| | | | | |
|---|---|---|---|---|
| 7,043,066 | B1 * | 5/2006 | Doi ......................... | G06T 5/50 382/132 |
| 2007/0276214 | A1 * | 11/2007 | Dachille ............... | G06T 7/0012 600/407 |
| 2009/0214099 | A1 * | 8/2009 | Merlet ..................... | G06T 7/11 382/132 |
| 2016/0012613 | A1 * | 1/2016 | Okerlund ............... | A61B 6/503 382/131 |
| 2016/0038246 | A1 * | 2/2016 | Wang ..................... | G16H 50/30 600/429 |

* cited by examiner

*Primary Examiner* — Fayyaz Alam

(57) ABSTRACT

A heart CT image processing method and apparatus and a non-transitory computer readable storage medium are provided in this application. The heart CT image processing method comprises reconstructing a heart CT image of a detected object based on projection data of a heart region of the detected object; processing voxel points having voxel values within a first threshold range in the heart CT image and obtaining a first image, wherein the first threshold range is defined by a CT value of a metal object; performing lung region segmentation on the first image to obtain a second image; performing initial heart region segmentation on the second image to obtain a third image; and performing rib removal on the third image to obtain a heart image.

12 Claims, 10 Drawing Sheets

HEART CT IMAGE PROCESSING METHOD AND APPARATUS, AND NON-TRANSITORY COMPUTER READABLE STORAGE MEDIUM

CROSS-REFERENCE TO RELATED APPLICATIONS

This application claims the benefit of Chinese Patent Application No. 2018-10696810.3 filed on Jun. 29, 2018, the disclosure of which is herein incorporated by reference in its entirety.

TECHNICAL FIELD

The present invention relates to image processing, and in particular, to a heart CT image processing method and apparatus, and a non-transitory computer readable storage medium.

BACKGROUND

Heart disease, especially coronary heart disease, is one of the major diseases that seriously impacts human health. Early detection of atherosclerotic plaques, aneurysms, and abnormal structures in the coronary arteries is an important factor in diagnosis and treatment of coronary heart disease. The detection of coronary heart disease mainly depends on a three-dimensional image of the heart of a detected object (for example, a patient), and therefore, one critical issue is how to accurately obtain a three-dimensional image of the heart of the detected.

The heart is located in the chest and between the two lungs. In the process of obtaining a three-dimensional image of the heart, adjacent tissues around the heart, such as the lungs and the ribs, must be removed. In the process of removing the adjacent tissues, if a metal object such as a pacemaker is present in the heart, or the detected object has undergone a thoracotomy such as a heart bypass surgery, when segmentation is performed on a CT image of the heart of the detected object, the metal object and its artifact will have a serious impact on the segmentation and generate inaccuracies in three-dimensional images of the heart For example, the three-dimensional images that only include part of the ribs or lung region, or the heart region obtained by the segmentation is incomplete. These inaccuracies will then impact the subsequent diagnosis of coronary arteries.

SUMMARY

A heart CT image processing method and apparatus, and a non-transitory computer readable storage medium are provided in the present invention.

The heart CT image processing method is provided in an exemplary embodiment of the present invention. The heart CT image processing method comprises reconstructing a heart CT image of a detected object based on projection data of a heart region of the detected object; processing voxel points having voxel values within a first threshold range in the heart CT image and obtaining a first image, wherein the first threshold range is defined by a CT value of a metal object; performing lung region segmentation on the first image to obtain a second image; performing initial heart region segmentation on the second image to obtain a third image; and performing rib removal on the third image to obtain a heart image.

A non-transitory computer readable storage medium is further provided in an exemplary embodiment of the present invention. The non-transitory computer readable storage medium is configured to store a computer program comprising instructions for performing the above heart CT image processing method.

A heart CT image processing apparatus is further provided in an exemplary embodiment of the present invention. The heart CT image processing apparatus comprises an image reconstruction module, a pre-processing module, a lung segmentation module, and an initial segmentation module. The image reconstruction module is configured to reconstruct a heart CT image of a detected object based on projection data of a heart region of the detected object. The pre-processing module is configured to process voxel points having voxel values within a first threshold range in the heart CT image and obtain a first image, wherein the first threshold range is defined by a CT value of a metal object. The lung segmentation module is configured to perform lung region segmentation on the first image to obtain a second image. The initial segmentation module is configured to perform initial heart region segmentation on the second image to obtain a third image. The rib removal module is configured to perform rib removal on the third image to obtain a heart image.

Other features and aspects will become clear through the following detailed description, accompanying drawings, and claims.

BRIEF DESCRIPTION OF THE DRAWINGS

The present invention can be better understood by describing exemplary embodiments of the present invention with reference to accompanying drawings introduced below.

DETAILED DESCRIPTION

Specific implementations of the present invention will be described below. It should be noted that during the specific description of the implementations, it is impossible to describe all features of the actual implementations in detail in this specification for the sake of brief description. It should be understood that in the actual implementation of any of the implementations, as in the process of any engineering project or design project, a variety of specific decisions are often made in order to achieve the developer's specific objectives and meet system-related or business-related restrictions, which will vary from one implementation to another. Moreover, it can also be understood that although the efforts made in such development process may be complex and lengthy, for those of ordinary skill in the art related to the disclosure of the present invention, some changes in design, manufacturing, production, or the like based on the technical content disclosed in this disclosure are only conventional technical means, and should not be construed as that the content of this disclosure is insufficient.

Unless otherwise defined, technical terms or scientific terms used in the claims and the description should be construed in the ordinary meanings that can be understood by those of ordinary skill in the art of the present invention. The words "first," "second," and similar words used in the description and claims of the present application for invention do not denote any order, quantity, or importance, but are merely used to distinguish different components. The word "one," "a/an," or a similar word does not denote a quantity limitation, but means that there is at least one. The word "include," "comprise," or a similar word is intended to mean that a component or an object that appears before the word "include" or "comprise" encompasses a component or an object and equivalent components that are listed after the word "include" or "comprise," and does not exclude other components or objects. The word "connect," "connected," or a similar word is not limited to a physical or mechanical connection, and is not limited to a direct or indirect connection.

In the present invention, the term "CT value" is a unit of measurement for determining the magnitude of the density of a local tissue or organ in a human body, and is commonly referred to as a Hounsfield unit (HU). The CT value can represent a pixel value or a voxel value.

Figure 1:
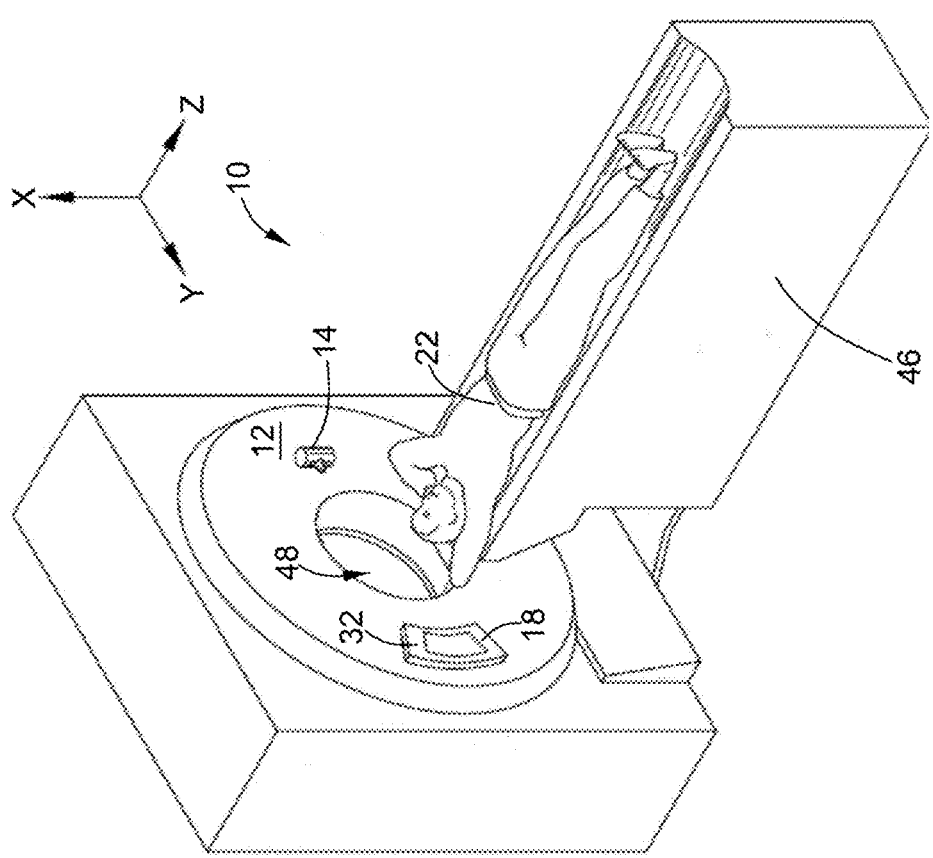
FIG. 1 is a schematic diagram of a CT system according to some embodiments of the present invention.

FIG. 1 is a schematic diagram of a CT system 10 according to an embodiment of the present invention. Referring to FIG. 1, the CT system 10 includes an X-ray source 14, a detector assembly 18, a carrying bed 46, and a control system (not shown). The X-ray source 14 and the detector assembly 18 are located on a rack 12. The detector assembly 18 consists of a plurality of detectors and a data acquisition system (DAS) 32. The plurality of detectors sense the intensity of attenuated X-rays that pass through a detected object 22 and generate analog electrical signals accordingly, and the data acquisition system 32 converts the analog electrical signals into digital signals for subsequent processing. During scanning to acquire X-ray projection data, the rack 12 and components mounted thereon (e.g., the X-ray source 14, the detector assembly 18, and the like) rotate about the center of a rack opening 48. The carrying bed 46 can move the detected object 22 to totally or partially pass through the rack opening 48.

Figure 2:
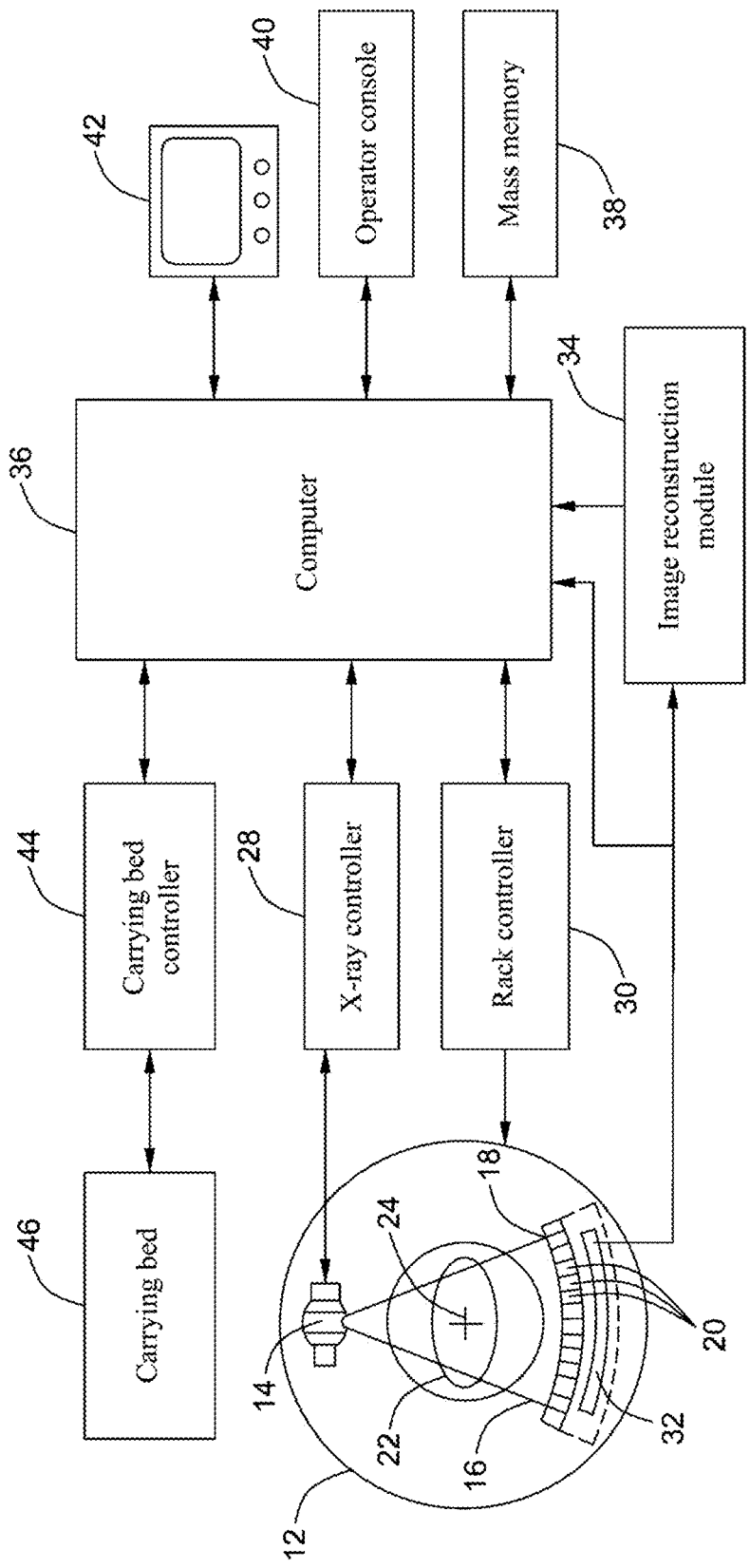
FIG. 2 is a schematic diagram of a control system in the CT system shown in FIG. 1.

FIG. 2 is a schematic diagram of a control system in the CT system shown in FIG. 1. As shown in FIG. 2, the control system includes an X-ray controller 28, a rack controller 30, and a carrying bed controller 44. The X-ray controller 28 controls operations of the X-ray source 14, the rack controller 30 controls operations of the rack 12, and the carrying bed controller 44 can control operations of the carrying bed 46.

The control system further includes an image reconstruction module 34. The image reconstruction module 34 can receive signals from the data acquisition system 32 and pre-process the signals to reconstruct a CT image of the detected object.

The control system further includes a computer 36. On one hand, the computer 36 can store the CT image generated by the image reconstruction module 34 and/or the projection data sent by the data acquisition system 32, store the CT image and/or the project data in a mass memory 38 that may include a computer RAM, a disk, and the like, and present the CT image and/or the project data to an operator through an associated display 42. On the other hand, the computer 36 can further be in communication connection with an operator console 40 to receive commands or scan parameters sent by the operator through an associated input device, so as to control the X-ray controller 28, the rack controller 30, and the carrying bed controller 44 to perform related operations. The associated input device includes a form of operator interface such as a keyboard, a mouse, a voice activated controller, or any other suitable input device.

In order to better detect and/or diagnose the coronary arteries, a three-dimensional image of the heart at the slowest systolic phase is required. When CT scanning is performed on the heart region of the detected object, the heartbeat of the detected object is simultaneously monitored to obtain a cardiogram of the detected object. In some embodiments, in order to obtain a three-dimensional image of the heart at the slowest systolic phase, CT scanning may be continuously performed on the detected object during the cardiac cycle to acquire projection data of the heart region of the detected object. At the image reconstruction stage, projection data of a suitable cardiac phase is selected based on the cardiogram to reconstruct a three-dimensional image of the heart. In some other embodiments, before the detected object is scanned, the slowest systolic phase of the detected object can be judged in advance. By monitoring the cardiogram of the detected object, the detected object is scanned during the prejudgment phase, to reconstruct a three-dimensional image of the heart based on the acquired projection data. In some non-limiting embodiments, there is a peak in the cardiogram, which is referred to as an R wave, and the slowest systolic phase is typically a period of time after the R wave. The heart CT image processing apparatus and method proposed by this application can perform heart segmentation on the three-dimensional image of the heart obtained in the above embodiment.

Figure 3:
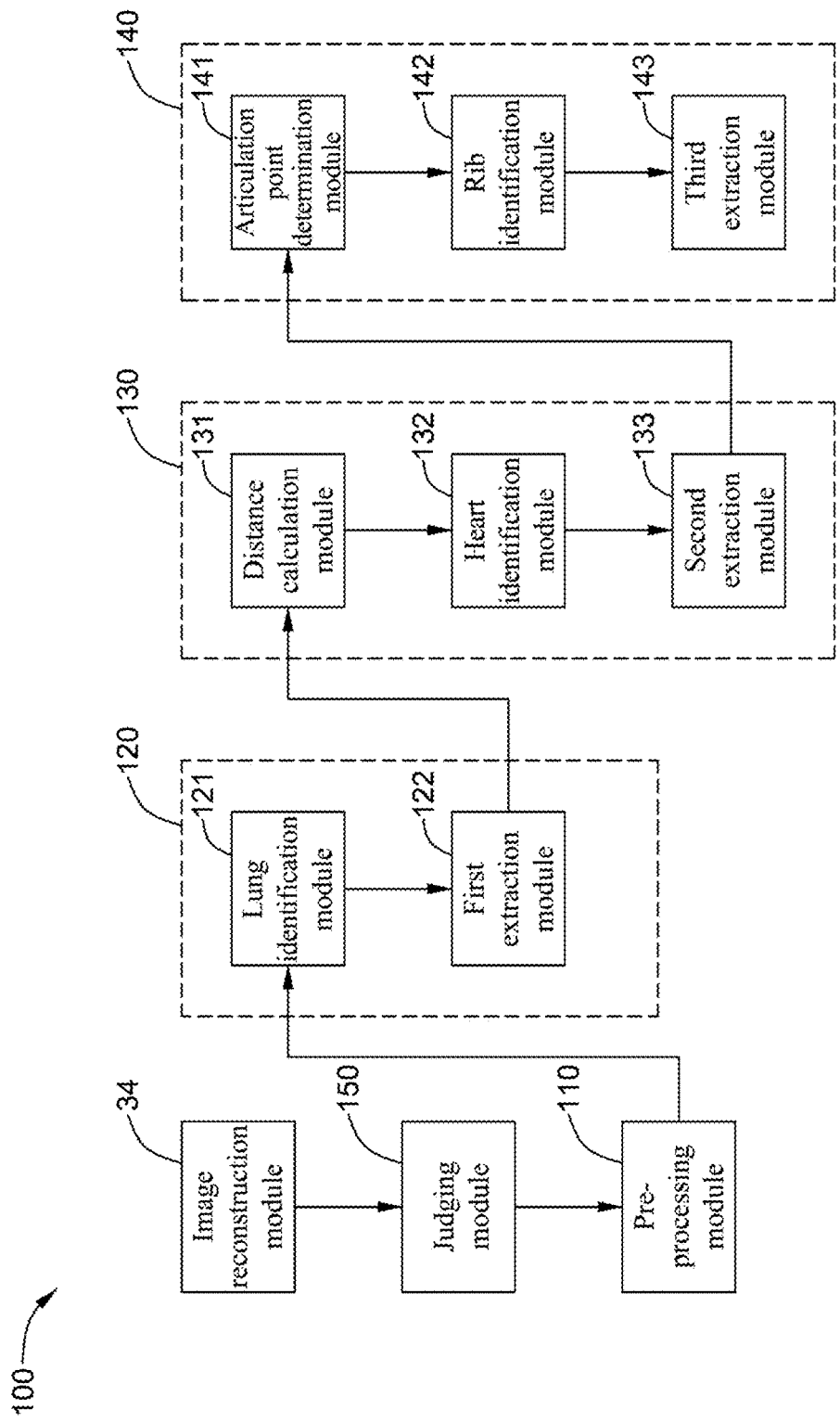
FIG. 3 is a schematic diagram of a heart CT image processing apparatus according to some embodiments of the present invention.
Figure 4:
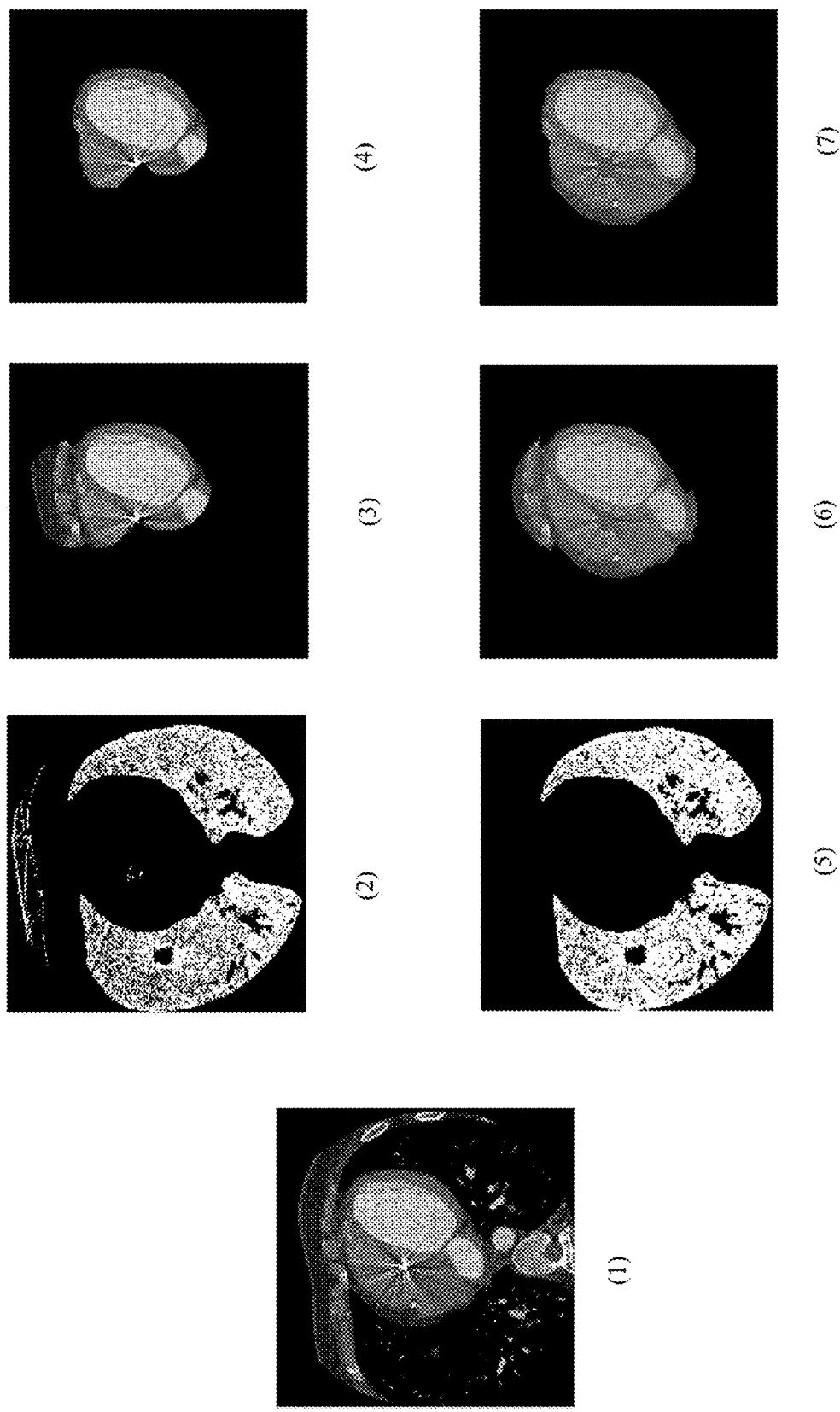
In FIG. 4, image (1) shows an initial heart CT image, images (2) to (4) show heart images obtained by performing heat segmentation without processing metal voxels in the prior art, and images (5) to (7) show heart images obtained by performing heart segmentation after voxel values of a metal object are replaced with a preset voxel value according to some embodiments of the present invention.

FIG. 3 is a schematic diagram of a heart CT image processing apparatus 100 according to some embodiments of the present invention. As shown in FIG. 3, the heart CT image processing apparatus 100 includes an image reconstruction module 34, a pre-processing module 110, a lung segmentation module 120, an initial segmentation module 130, and a rib removal module 140. The image reconstruction module 34 is configured to reconstruct a heart CT image of a detected object based on projection data of a heart region of the detected object. The pre-processing module 110 is configured to process voxel points having voxel values within a first threshold range in the heart CT image and obtain a first image, wherein the first threshold range is defined by a CT value of a metal object. In some embodiments, the pre-processing module 110 is configured to replace the voxel values within the first threshold range with a preset voxel value to avoid the effect of a metal object present in the heart on heart segmentation. In some embodiments, the preset voxel value includes a CT value of water or another substance. Preferably, the preset voxel value is a CT value of water, for example, 0 HU. In this way, poor precision of heart identification due to a metal artifact, e.g., problems such as a large center offset or a large loss of the heart, can be avoided. In FIG. 4, image (1) shows an initial heart CT image, images (2) to (4) show heart images obtained by performing heart segmentation without processing metal voxels according to the prior art, and images (5) to (7) show heart images obtained by performing heart segmentation after voxel values of a metal object are replaced with a voxel value of water, for example, according to the present invention. As can be seen from images (2) to (4) in FIG. 4, the metal artifact in the middle is mistakenly identified as the lung tissue, so that a determined heart center has a great offset compared with the actual center, and a heart image obtained after the segmentation is thus incomplete. As can be seen from images (5) to (7) in FIG. 4, the accuracy of heart segmentation is greatly improved due to the removal of the metal artifact.

Figure 5:
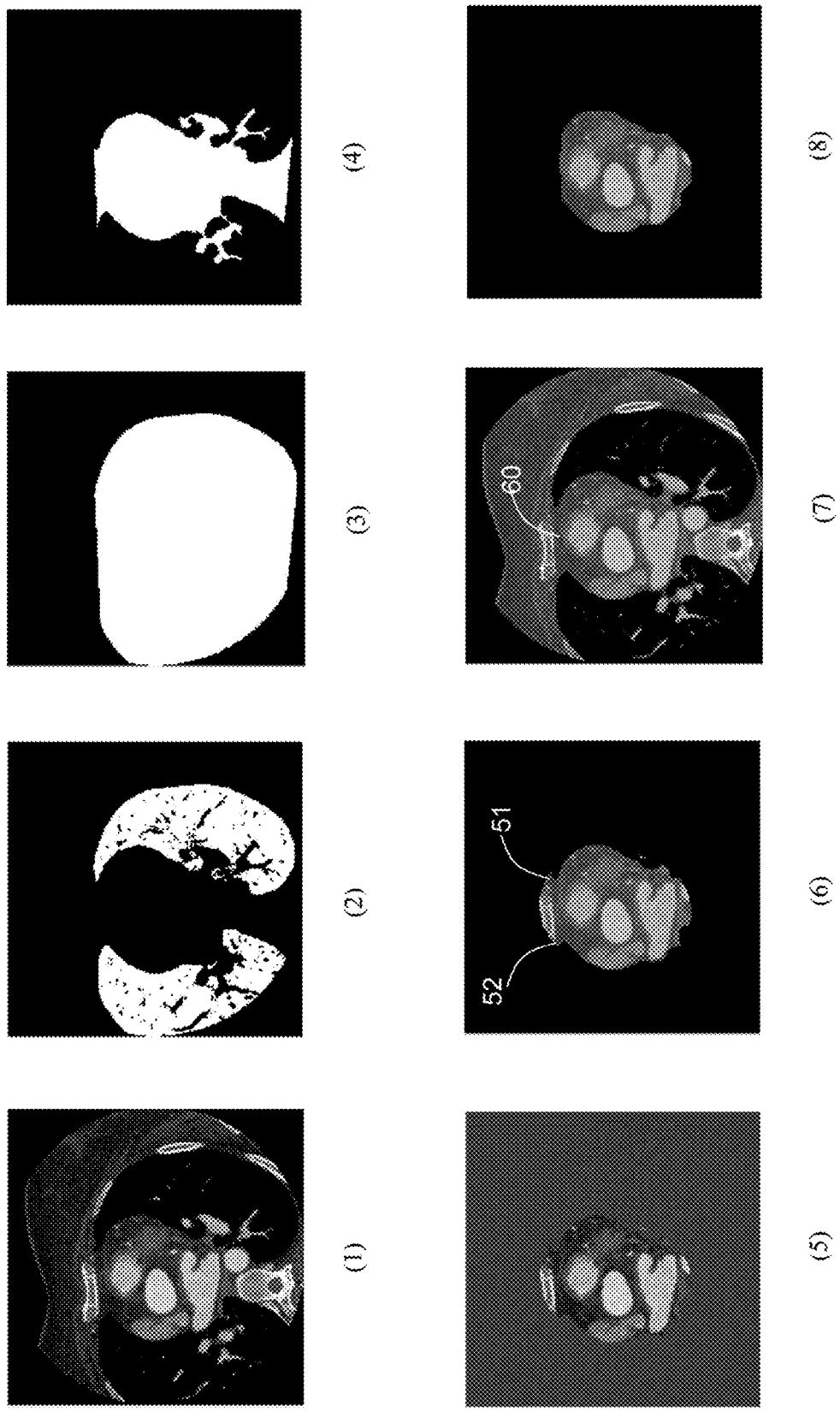
In FIG. 5, images (1) to (8) respectively show some intermediate images during the processing of a heart CT image processing apparatus according to some embodiments of the present invention.

In some embodiments, the pre-processing module 110 processes the heart CT image based on a binary method to obtain a first image, as shown by image (1) in FIG. 5. The lung segmentation module 120 is configured to perform lung region segmentation on the first image to obtain a second image. The initial segmentation module 130 is configured to perform initial heart region segmentation on the second image to obtain a third image, as shown by image (6) in FIG. 5. The rib removal module 140 is configured to perform rib removal on the third image to obtain a heart image, as shown by image (8) in FIG. 5.

In some non-limiting embodiments, the heart CT image processing apparatus 100 further includes a judging module 150, configured to judge whether a metal object is present in the heart of the detected object based on the voxel values in the heart CT image. Generally, a CT value of the metal object defines a first threshold range, and the first threshold range may be set larger in order to better judge whether a metal object is present in the heart of the detected object. In some embodiments, the judging module 150 can judge whether a metal object is present in the heart of the detected object by judging whether there are a proportion of voxel values in the heart CT image reconstructed by the image reconstruction module 34 that are within the first threshold range. In some embodiments, the judging module 150 is connected to the pre-processing module 110. Namely, regardless of whether the judging module 150 judges that a metal object is present or absent in the heart of the detected object, the pre-processing module 110 processes the voxel points having voxel values in the first threshold range in the heart CT image and obtains the first image. The judging module 150 judging that no metal object is present in the detected object is equivalent to having no voxel point within the first threshold range in the heart CT image, hence the first image obtained by the pre-processing module 110 is the heart CT image.

In some other embodiments, the heart CT image processing apparatus 100 may not include the judging module 150. The heart CT image processing apparatus 100 may be in communication connection with an operator console 40 through the computer 36 in the CT system as shown in FIG. 2. An operator can input through an associated input device that a pacemaker or another metal object is present in the detected object, and the processing apparatus 100 can receive the signal and perform subsequent operations on the heart CT image.

In some embodiments, the lung segmentation module 120 includes a lung identification module 121 and a first extraction module 122.

The lung identification module 121 is connected to the pre-processing module 110, and is configured to identify a region of voxel points having voxel values within a second threshold range in the first image obtained by the pre-processing module 110 as a lung region (e.g., the identified lung region is shown in image (2) of FIG. 5), and further identify a convex hull of the lung region. In some embodiments, the second threshold range is defined by a CT value of the lung region. In some embodiments, the lung identification module 121 is configured to determine the convex hull of the lung region based on a convex hull algorithm. In some other embodiments, the lung identification module 121 can also determine the convex hull of the lung region based on other suitable algorithms. For example, image (3) in FIG. 5 can be obtained by identifying the convex hull of the lung region.

The first extraction module 122 is connected to the lung identification module 121, and is configured to extract the convex hull identified by the lung identification module 121 and an internal region thereof to obtain the second image. In some embodiments, the internal region of the convex hull includes the lung region, the heart region, ribs, and the like. For example, image (2) in FIG. 5 shows the lung region, and image (4) in FIG. 5 shows the internal region of the lungs. Through the identification and extraction of the lung region, the problem of inaccurate heart segmentation due to the influence of the chest wall (for example, the tissue located at the periphery of the lungs in image (1) in FIG. 5) can be avoided.

In some embodiments, the initial segmentation module 130 includes a distance calculation module 131, a heart identification module 132, and a second extraction module 133.

The distance calculation module 131 is connected to the first extraction module 122 and is configured to calculate, based on the second image, distances from each of voxel points that are not located in the lung region to all voxel points in the lung region, and obtain the shortest distance corresponding to each of the voxel points. In some embodiments, the distance calculation module 131 can calculate a Euclidean distance from each voxel point in a non-lung region to a point in the lung region the most adjacent to the voxel point. For example, a calculation formula of a Euclidean distance $D_1$ from any voxel point $(x_1, y_1, z_1)$ in the non-lung region to a voxel point $(x'_1, y'_1, z'_1)$ in the lung region the most adjacent to the voxel point is as follows:

$$D_1 = \sqrt{(x_1-x'_1)^2 + (y_1-y'_1)^2 + (z_1-z'_1)^2}$$

In other words, in the second image, all voxel points $((x_1, y_1, z_1) \sim (x_n, y_n, z_n))$ in the non-lung region each correspond to a shortest Euclidean distance $D_1 \sim D_n$.

The heart identification module 132 is configured to identify a region where voxel points corresponding to shortest distances greater than or equal to a preset threshold in the non-lung region are located as an initial heart region. In some embodiments, the preset threshold is determined according to the maximum value among the shortest distances corresponding to the voxel points that are not located in the lung region and a predetermined proportionality coefficient. For example, a preset threshold T is determined based on the maximum value $\max(D_1 \sim D_n)$ among the shortest Euclidean distances $D_1 \sim D_n$ and proportionality coefficients $\alpha$ and $\beta$ according to the following formula:

$$T=(1+\beta)\cdot\alpha\cdot\max(D_1 \sim D_n)$$

Here, $\alpha$ and $\beta$ are both constants, and by selecting suitable values of $\alpha$ and $\beta$, it can be ensured that the identified initial heart region maintains the shape of the heart while removing the parts of the ribs and the spine as much as possible.

In some other embodiments, the preset threshold may be determined according to one proportionality coefficient. In some other embodiments, the preset threshold may be determined according to other formulas.

Image (5) in FIG. 5 shows the identified and extracted initial heart region. It can be seen from image (5) that compared with image (4), a non-heart portion, e.g., the spine, at the lower part of image (4) is removed.

The second extraction module 133 is configured to extract the convex hull and the initial heart region to obtain the third image.

In some embodiments, the rib removal module 140 includes an articulation point determination module 141, a rib identification module 142, and a third extraction module 143.

The articulation point determination module 141 is configured to obtain a first pair of rib articulation points according to a tangent point of the convex hull and the initial heart region, e.g., two points 51 and 52 represented by the symbol "*" in image (6) in FIG. 5 (the symbol "*" is used for illustration only to facilitate description, and in practice, the points may not be labeled or may be labeled in other forms), and correspondingly finds, in the third image, a second pair of rib articulation points having the shortest distance to the first pair of rib articulation points and voxel values within a third threshold range. In some embodiments, the third threshold range is defined based on a CT value of fat. In some non-limiting embodiments, there is a first rib articulation point on each of the left and right sides of the third image. One second rib articulation point that meets the condition can be found near the first rib articulation point on the left side, and the other second rib articulation point that meets the condition can be found near the first rib articulation point on the right side. For example, when a voxel value of the first rib articulation point is 1000, a point closest to the first rib articulation point and having a voxel value unequal to 1000 is found as the second rib articulation point.

The rib identification module 142 is configured to determine the shortest path between the second pair of rib articulation points. In some embodiments, a rule for determining the shortest path is that the path does not pass through the heart region nor through a rib structure. In some embodiments, the rib identification module 142 can further determine the shortest path between the first pair of rib articulation points. In some embodiments, the rib identification module 142 can determine the shortest path based on a Dijkstra algorithm. In some other embodiments, the rib identification module 142 can further determine a connection line between the rib articulation points based on other algorithms. A connection line 60 in image (7) in FIG. 5 shows the shortest path between the second pair of rib articulation points obtained in one implementation.

The third extraction module 143 is configured to remove the convex hull, the shortest path, and a region therebetween from the third image to obtain a heart image. In some embodiments, if the rib identification module 142 further determines the shortest path between the first pair of rib articulation points, the third extraction module 143 can further remove the convex hull, the shortest path between the first pair of rib articulation points, and a region therebetween from the third image to obtain a heart image as shown in image (8) of FIG. 5.

Figure 6:
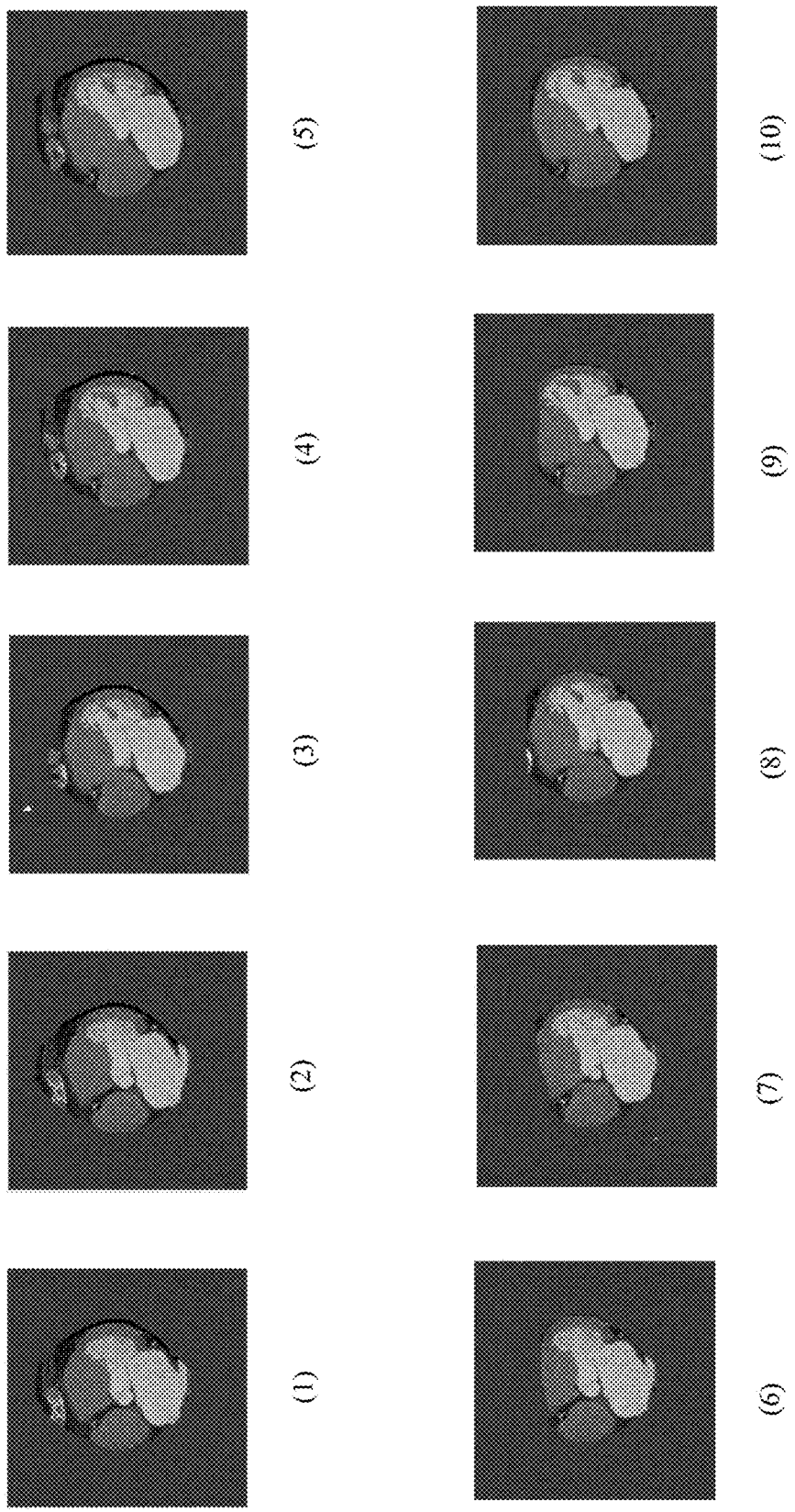
In FIG. 6, images (1) to (5) show heart images obtained by performing heart segmentation through a rib removing method in the prior art, and images (6) to (10) show heart images corresponding to images (1) to (5) and obtained by performing heart segmentation through a rib removing method according to some embodiments of the present invention.

In FIG. 6, images (1) to (5) show heart images obtained by performing heart segmentation through a rib removing method according to the prior art, and images (6) to (10) show heart images corresponding to images (1) to (5) and obtained by performing heart segmentation through a rib removing method according to some embodiments of the present invention. It can be found through comparison that the rib removal module 140 proposed by this application can better remove the ribs more accurately while maintaining the complete heart region.

Figure 7:
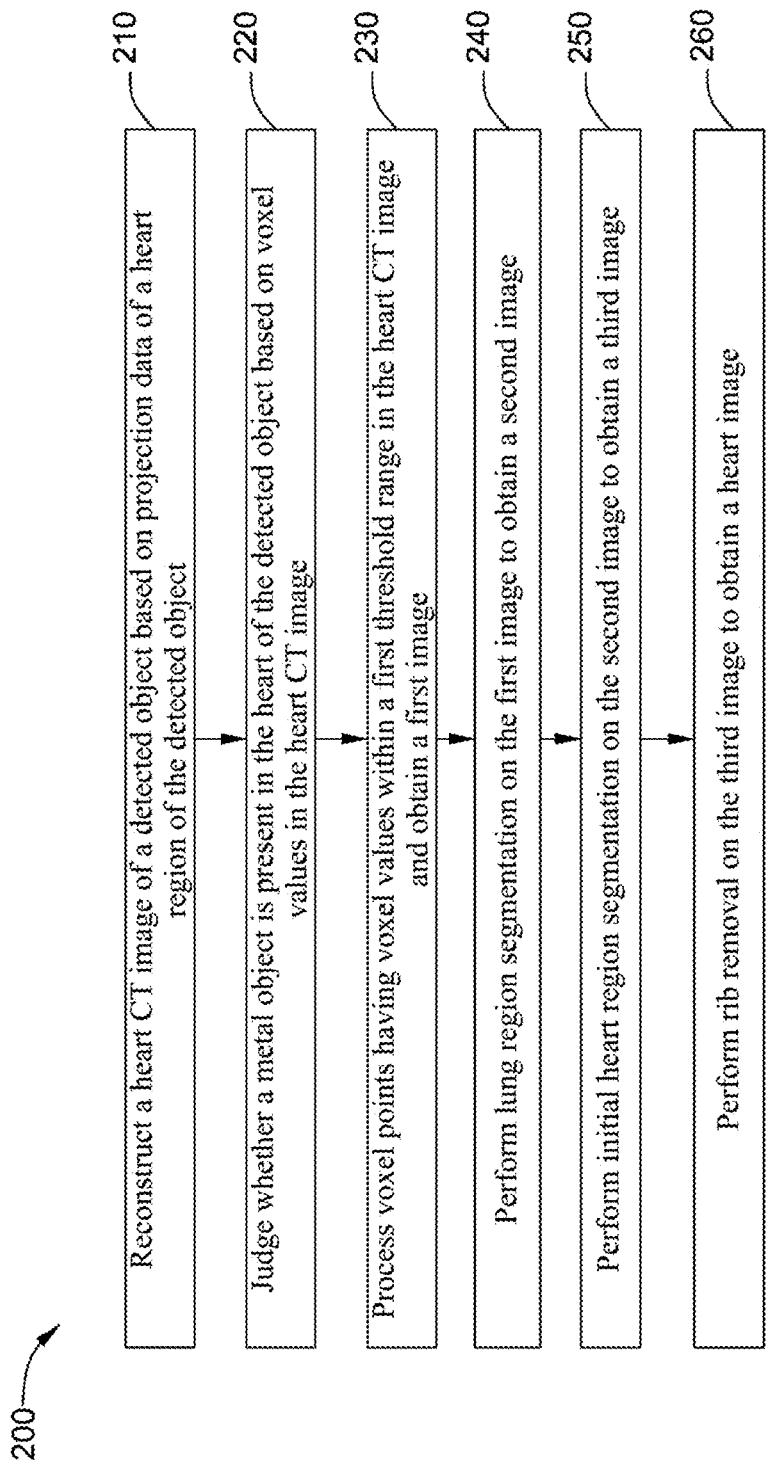
FIG. 7 is a flowchart of a heart CT image processing method according to some embodiments of the present invention.

FIG. 7 is a flowchart of a heart CT image processing method 200 according to some embodiments of the present invention. As shown in FIG. 7, the heart CT image processing method 200 includes the following steps:

In step 210, a heart CT image of a detected object is reconstructed based on projection data of a heart region of the detected object.

Optionally, the heart CT image processing method 200 further includes a step 220 of judging whether a metal object is present in the heart of the detected object based on voxel values in the heart CT image. In some embodiments, it is judged whether a metal object is present in the heart of the detected object by judging whether there are a certain proportion of voxel values in the heart CT image that are within a first threshold range. In some embodiments, the first threshold range is defined by a CT value of the metal object.

In step 230, voxel points having voxel values within the first threshold range in the heart CT image are processed and a first image is obtained, wherein the first threshold range is defined by the CT value of the metal object. In some embodiments, the processing voxel points having voxel values within the first threshold range in the heart CT image include replacing the voxel values within the first threshold range with a preset voxel value to avoid the effect of a metal object present in the heart on heart segmentation. In some embodiments, the preset voxel value includes a CT value of water or another substance. Preferably, the preset voxel value is 0 HU. In some embodiments, the heart CT image can be processed based on a binary method to obtain the first image.

In step 240, lung region segmentation is performed on the first image to obtain a second image.

In step 250, initial heart region segmentation is performed on the second image to obtain a third image.

In step 260, rib removal is performed on the third image to obtain a heart image.

Figure 8:
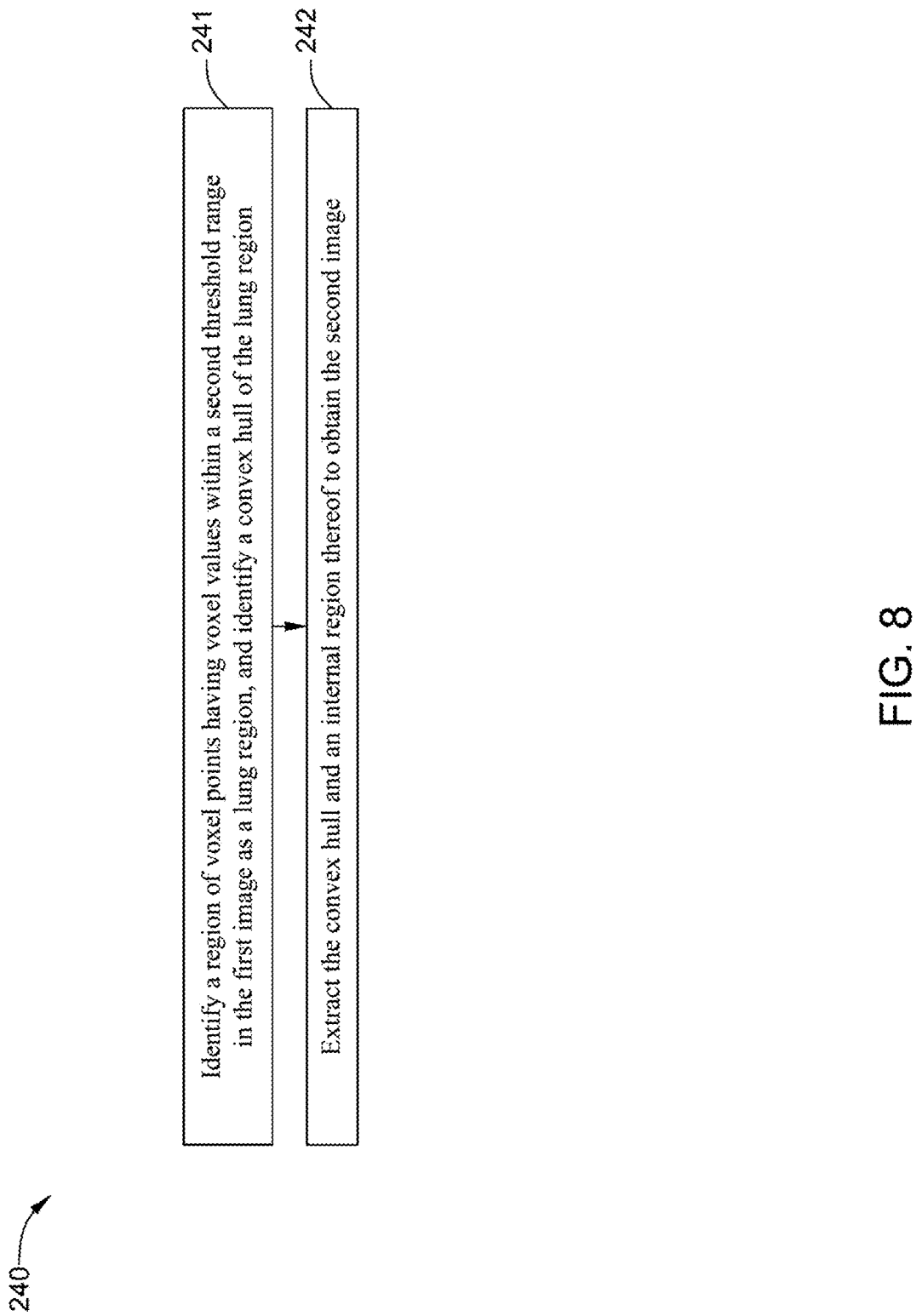
FIG. 8 is a flowchart of step 240 according to the method shown in FIG. 7.

FIG. 8 is a flowchart of step 240 in the method shown in FIG. 7. As shown in FIG. 8, step 240 includes the following steps.

In step 241, a region of voxel points having voxel values within a second threshold range in the first image is identified as a lung region, and a convex hull of the lung region is identified. In some embodiments, the second threshold range is defined by a CT value of the lung region. In some embodiments, the convex hull of the lung region is determined through a convex hull algorithm.

In step 242, the convex hull and an internal region thereof are extracted to obtain the second image. In some embodiments, the internal region of the convex hull includes the lung region, the heart region, ribs, and the like. In some embodiments, extracting the convex hull and the internal region thereof is equivalent to removing a region outside the convex hull (e.g., the chest wall), thus avoiding an inaccurate result of heart segmentation caused by classifying some voxel points in, for example, the chest wall into the initial heart region.

Figure 9:
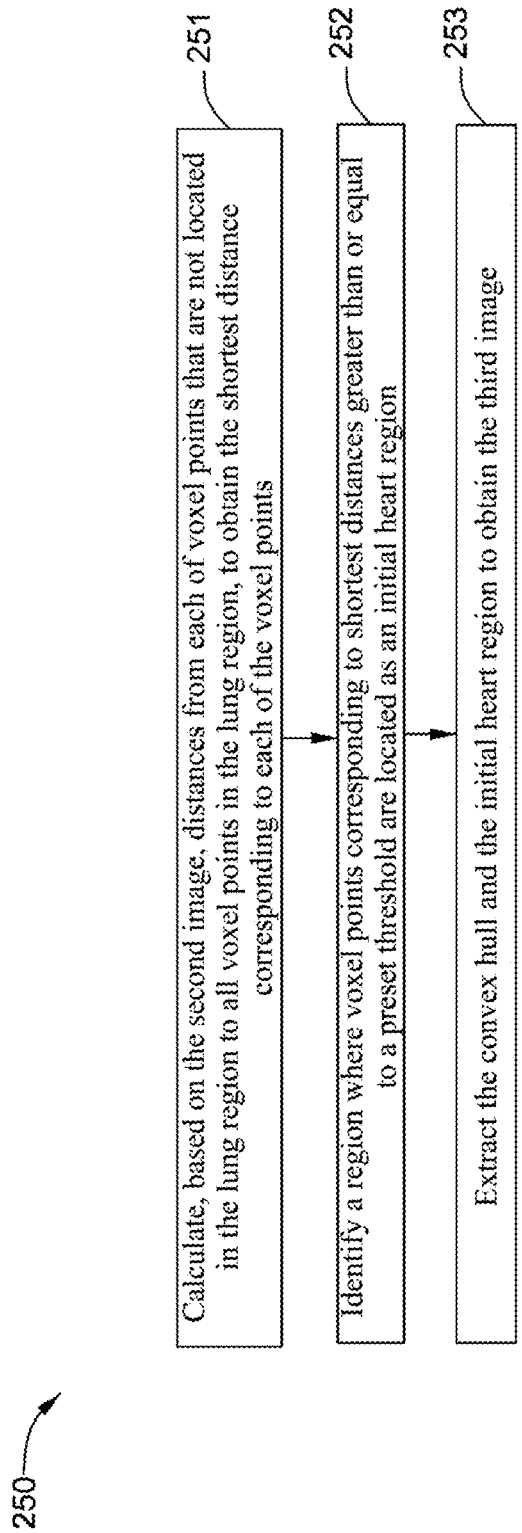
FIG. 9 is a flowchart of step 250 according to the method shown in FIG. 7.

FIG. 9 is a flowchart of step 250 in the method shown according to FIG. 7. As shown in FIG. 9, step 250 includes the following steps.

In step 251, distances from each of voxel points that are not located in the lung region to all voxel points in the lung region are calculated based on the second image to obtain the shortest distance corresponding to each of the voxel points. In some embodiments, the shortest distance $D_1$ can be calculated according to the following formula:

$$D_1 = \sqrt{(x_1-x'_1)^2+(y_1-y'_1)^2+(z_1-z'_1)^2}$$

Here, $(x_1, y_1, z_1)$ is any voxel point in a non-lung region, and $(x'_1, y'_1, z'_1)$ is a voxel point in the lung region that is closest to the voxel point $(x_1, y_1, z_1)$.

In step 252, a region where voxel points corresponding to shortest distances greater than or equal to a preset threshold are located is identified as an initial heart region. In some embodiments, the preset threshold is a product of the maximum value among the shortest distances corresponding to the voxel points that are not located in the lung region and a predetermined proportionality coefficient.

In step 253, the convex hull and the initial heart region are extracted to obtain the third image.

Figure 10:
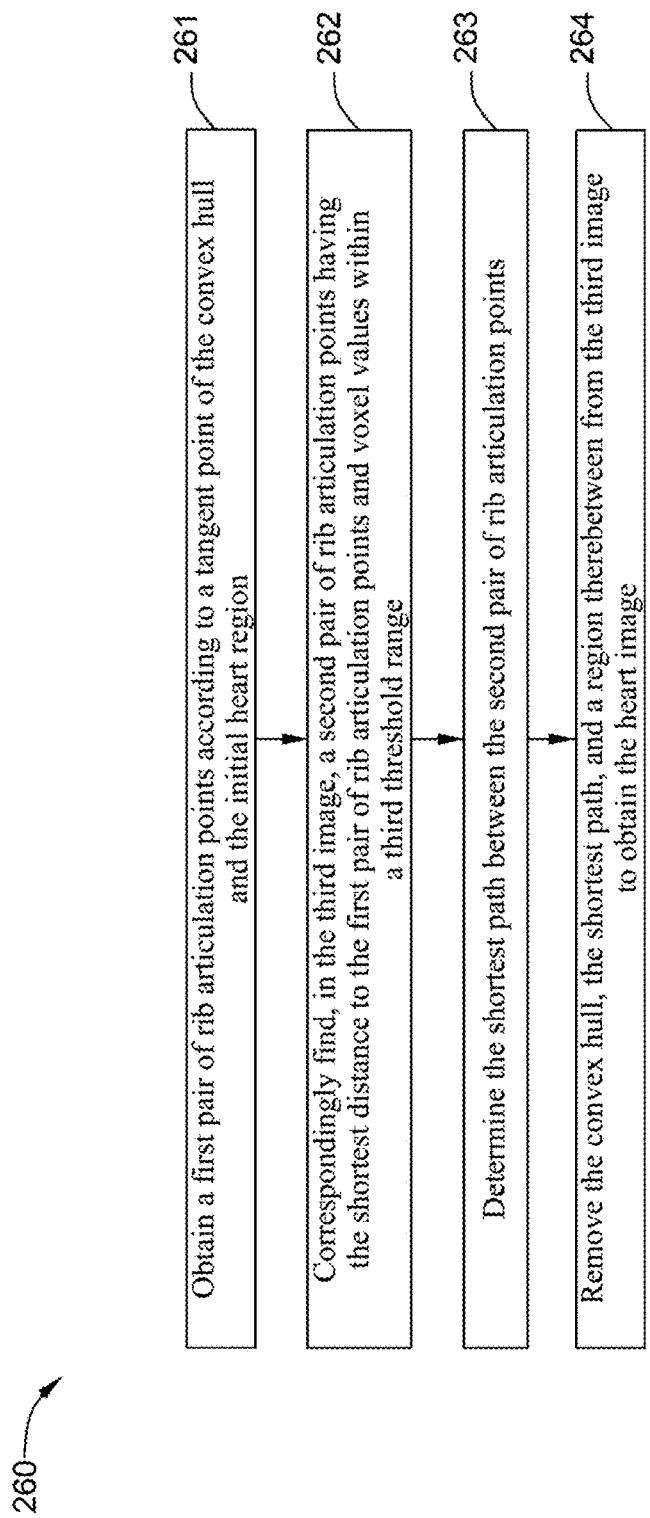
FIG. 10 is a flowchart of step 260 according to the method shown in FIG. 7.

FIG. 10 is a flowchart of step 260 in the method shown according to FIG. 7. As shown in FIG. 10, step 260 includes the following steps.

In step 261, a first pair of rib articulation points is obtained according to a tangent point of the convex hull and the initial heart region.

In step 262, a second pair of rib articulation points having the shortest distance to the first pair of rib articulation points and voxel values within a third threshold range is correspondingly found in the third image. In some embodiments, the third threshold range is defined based on a CT value of fat.

In step 263, the shortest path between the second pair of rib articulation points is determined. In some embodiments, the shortest path is determined based on a Dijkstra algorithm. In some embodiments, a rule for determining the shortest path is that the path does not pass through the heart region nor through a rib structure. In some embodiments, the shortest path between the first pair of rib articulation points can further be determined.

In step 264, the convex hull, the shortest path, and a region therebetween are removed from the third image to obtain a heart image. In some embodiments, the convex hull, the shortest path between the first pair of rib articulation points, and a region therebetween can further be removed.

The heart CT image processing method proposed by this application can better obtain a three-dimensional image of the heart of a detected object by segmentation in the presence of a metal object in the heart of the detected object, and can remove the ribs more precisely by improving a rib removal algorithm while maintaining the complete structure of the heart, thus providing a powerful reference for the detection and/or diagnosis of coronary arteries.

A non-transitory computer readable storage medium can further be provided in the present invention. The non-transitory computer readable storage medium is configured to store an instruction set and/or a computer program. When executed by a computer, the instruction set and/or computer program causes the computer to perform of the above heart CT image processing method. The computer executing the instruction set and/or computer program may be a computer of a CT system, such as the computer 36 in FIG. 2. In one embodiment, the instruction set and/or computer program can be programmed into a processor/controller of the computer 36.

Specifically, when executed by the computer, the instruction set and/or computer program causes the computer to:
reconstruct a heart CT image of a detected object based on projection data of a heart region of the detected object;
process voxel points having voxel values within a first threshold range in the heart CT image and obtain a first image;
perform lung region segmentation on the first image to obtain a second image;
perform initial heart region segmentation on the second image to obtain a third image; and
perform rib removal on the third image to obtain a heart image.

The instructions as described above may be combined into one instruction for execution, and any of the instructions may also be split into a plurality of instructions for execution. Moreover, the execution order is also not limited to the instruction execution order as described above.

In some embodiments, the instruction set and/or computer program further causes the computer to:
judge whether a metal object is present in the heart of the detected object based on the voxel values in the heart CT image.

In some embodiments, the performing lung region segmentation on the first image to obtain a second image may include:
identifying a region of voxel points having voxel values within a second threshold range in the first image as a lung region, and identifying a convex hull of the lung region; and
extracting the convex hull and an internal region thereof to obtain the second image.

In some embodiments, the instruction 4 includes the following instructions for:
calculating, based on the second image, distances from each of voxel points that are not located in the lung region to all voxel points in the lung region, to obtain the shortest distance corresponding to each of the voxel points;
identifying a region where voxel points corresponding to shortest distances greater than or equal to a preset threshold are located as an initial heart region; and
extracting the convex hull and the initial heart region to obtain a third image.

In some embodiments, the performing rib removal on the third image to obtain a heart image may include:
obtaining a first pair of rib articulation points according to a tangent point of the convex hull and the initial heart region;
correspondingly finding, in the third image, a second pair of rib articulation points having the shortest distance to the first pair of rib articulation points and voxel values within a third threshold range;
determining the shortest path between the second pair of rib articulation points; and
removing the convex hull, the shortest path, and a region therebetween from the third image to obtain the heart image.

As used herein, the term "computer" may include any processor-based or microprocessor-based system including a system that uses a microcontroller, a reduced instruction set computer (RISC), an application specific integrated circuit (ASIC), a logic circuit, and any other circuit or processor capable of performing the functions described herein. The above examples are merely exemplary and thus are not intended to limit the definition and/or meaning of the term "computer" in any way.

The instruction set may include various commands that instruct a computer acting as a processor or a processor to perform particular operations, such as the methods and processes of various embodiments. The instruction set may be in the form of a software program, and the software program can form a part of one or more tangible, non-transitory computer readable media. The software may be in various forms such as system software or application software. In addition, the software may be in the form of a set of independent programs or modules, a program module within a larger program, or a part of a program module. The software can also include modular programming in the form of object-oriented programming. The input data may be processed by the processor in response to an operator command, or in response to a previous processing result, or in response to a request made by another processor.

Some exemplary embodiments have been described above; however, it should be understood that various modifications may be made. For example, if the described techniques are performed in a different order and/or if the components of the described system, architecture, device, or circuit are combined in other manners and/or replaced by or supplemented with additional components or equivalents thereof, a suitable result can be achieved. Accordingly, other implementations also fall within the protection scope of the claims.

The invention claimed is:

1. A heart CT image processing method, comprising:
reconstructing a heart CT image of a detected object based on projection data of a heart region of the detected object;
processing voxel points having voxel values within a first threshold range in the heart CT image and obtaining a first image, wherein the first threshold range is defined by a CT value of a metal object;
performing lung region segmentation on the first image to obtain a second image;
performing initial heart region segmentation on the second image to obtain a third image; and
performing rib removal on the third image to obtain a heart image.

2. The method according to claim 1, wherein the processing voxel points having voxel values within a first threshold range in the heart CT image comprises replacing the voxel values within the first threshold range with a preset voxel value.

3. The method according to claim 1, wherein the method further comprises:
judging whether a metal object is present in the heart of the detected object based on the voxel values in the heart CT image.

4. The method according to claim 1, wherein the lung region segmentation comprises:
identifying a region of voxel points having voxel values within a second threshold range in the first image as a lung region and identifying a convex hull of the lung region; and
extracting the convex hull and an internal region thereof to obtain the second image.

5. The method according to claim 4, wherein the initial heart region segmentation comprises:
calculating, based on the second image, distances from each of voxel points that are not located in the lung region to all voxel points in the lung region, to obtain the shortest distance corresponding to each of the voxel points;
identifying a region where voxel points corresponding to shortest distances greater than or equal to a preset threshold are located as an initial heart region; and
extracting the convex hull and the initial heart region to obtain the third image.

6. The method according to claim 5, wherein the preset threshold is a product of the maximum value among the shortest distances corresponding to the voxel points that are not located in the lung region and a predetermined proportionality coefficient.

7. The method according to claim 5, wherein the rib removal comprises:
obtaining a first pair of rib articulation points according to a tangent point of the convex hull and the initial heart region;
correspondingly finding, in the third image, a second pair of rib articulation points having the shortest distance to the first pair of rib articulation points and voxel values within a third threshold range;
determining the shortest path between the second pair of rib articulation points; and
removing the convex hull, the shortest path, and a region therebetween from the third image to obtain the heart image.

8. A non-transitory computer readable storage medium, configured to store a computer program, wherein when executed by a computer, the computer program causes the computer to perform the heart CT image processing method of claim 1.

9. A heart CT image processing apparatus, comprising:
an image reconstruction module, configured to reconstruct a heart CT image of a detected object based on projection data of a heart region of the detected object;
a pre-processing module, configured to process voxel points having voxel values within a first threshold range in the heart CT image and obtain a first image, wherein the first threshold range is defined by a CT value of a metal object;
a lung segmentation module, configured to perform lung region segmentation on the first image to obtain a second image;
an initial segmentation module, configured to perform initial heart region segmentation on the second image to obtain a third image; and
a rib removal module, configured to perform rib removal on the third image to obtain a heart image.

10. The apparatus according to claim 9, wherein the lung segmentation module comprises:
a lung identification module, configured to identify a region of voxel points having voxel values within a second threshold range in the first image as a lung region, and identify a convex hull of the lung region; and
a first extraction module, configured to extract the convex hull and an internal region thereof to obtain the second image.

11. The apparatus according to claim 10, wherein the initial segmentation module comprises:
a distance calculation module, configured to calculate, based on the second image, distances from each of voxel points that are not located in the lung region to all voxel points in the lung region and obtain the shortest distance corresponding to each of the voxel points;

a heart identification module, configured to identify a region where voxel points corresponding to shortest distances greater than or equal to a preset threshold are located as an initial heart region; and a second extraction module, configured to extract the convex hull and the initial heart region to obtain the third image.

12. The apparatus according to claim 11, wherein the rib removal module comprises:

an articulation point determination module, configured to obtain a first pair of rib articulation points according to a tangent point of the convex hull and the initial heart region, and correspondingly find, in the third image, a second pair of rib articulation points having the shortest distance to the first pair of rib articulation points and voxel values within a third threshold range;

a rib identification module, configured to determine the shortest path between the second pair of rib articulation points; and a third extraction module, configured to remove the convex hull, the second shortest path, and a region therebetween from the third image to obtain the heart image.

* * * * *